United States Patent [19]

Oude Alink

[11] 4,145,545
[45] Mar. 20, 1979

[54] PROCESS FOR PREPARING TETRAHYDROPYRIMIDINES

[75] Inventor: Bernardus A. Oude Alink, St. Louis, Mo.

[73] Assignee: Petrolite Corporation, St. Louis, Mo.

[21] Appl. No.: 806,878

[22] Filed: Jun. 15, 1977

Related U.S. Application Data

[63] Continuation of Ser. No. 292,494, Sep. 27, 1972, Pat. No. 4,085,084.

[51] Int. Cl.² ............................................ C07D 239/06
[52] U.S. Cl. .................................................. 544/242
[58] Field of Search ..................... 260/251 R; 544/242

[56] References Cited

U.S. PATENT DOCUMENTS

| | | | |
|---|---|---|---|
| 3,904,625 | 9/1975 | Alink | 260/251 R |
| 3,943,134 | 3/1976 | Kajiyama et al. | 260/251 R |
| 4,085,104 | 4/1978 | Alink | 544/242 |

*Primary Examiner*—Nicholas S. Rizzo
*Attorney, Agent, or Firm*—Sidney B. Ring; Hyman F. Glass

[57] ABSTRACT

Substituted 2, 3, 4, 5-tetrahydropyridimines (THP)

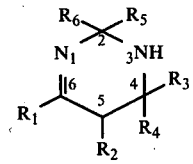

are prepared as follows:
  (1) The reaction of a carbonyl compound (ketone or aldehyde) with ($NH_3$ or $NH_4OH$) and a sulfur-containing catalyst.
  (2) The reaction of an $\alpha$, $\beta$-unsaturated ketone and a carbonyl compound and $NH_3$ (or $NH_4OH$) without a catalyst.
  (3) Reaction of an $\alpha$, $\beta$-unsaturated ketone, a 1-amino-alcohol and $NH_3$ (or $NH_4OH$) without a catalyst.

The compositions of this invention react with carbon disulfide to form xanthates, can be isomerized, converted to pyridines, etc.

THP and derivatives of this invention are useful as biocides, anti-oxidants, oxygen scavengers, corrosion inhibitors, etc.

8 Claims, No Drawings

PROCESS FOR PREPARING TETRAHYDROPYRIMIDINES

This is a continuation of application Ser. No. 292,494, filed Sept. 27, 1972, now U.S. No. 4,085,104.

This invention relates to tetrahydropyrimidines (THP), to the preparation thereof with or without novel catalysts; uses thereof; and to derivatives thereof.

THP is prepared by the following procedures:

I

Reaction of a carbonyl compound (aldehyde or ketone) with ammonia according to the general reaction

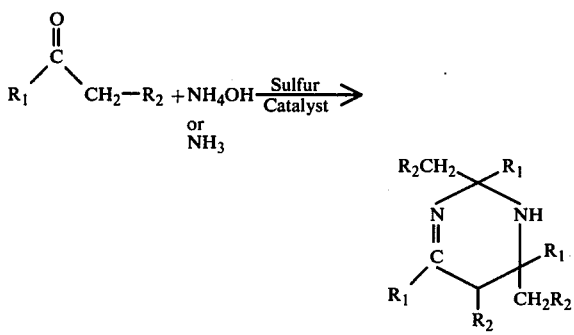

II

Reaction of an α, β unsaturated ketone with ammonia and a carbonyl compound (aldehyde or ketone) according to the general reaction

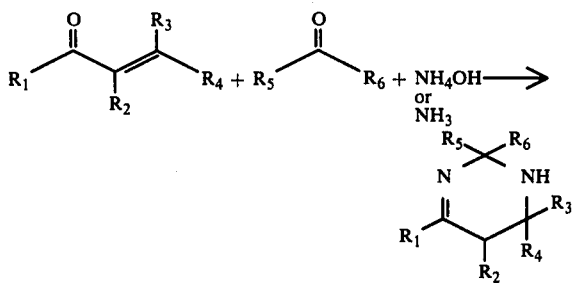

III

Reaction of an unsaturated carbonyl compound (aldehyde or ketone) with a 1-aminoalcohol and ammonia according to the general reaction

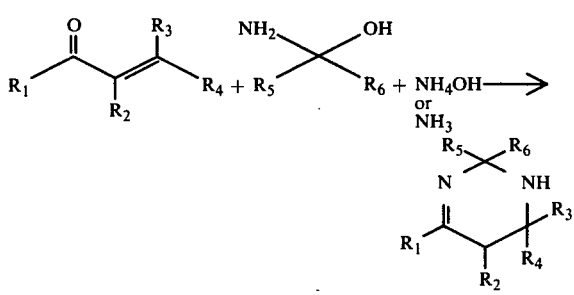

$R_1$, $R_2$, $R_3$, $R_4$, $R_5$ and $R_6$, which may be the same or different, are hydrogen or substituted group such as alkyl, aryl, cycloalkyl, alkaryl, aralkyl, heterocyclic, substituted derivatives thereof, etc. In addition R groups may be joined in a cyclic configuration which makes the THP structure a part of the substituted group.

Alkyl includes methyl, ethyl, propyl, butyl, amyl, hexyl, heptyl, octyl, nonyl, decyl, undecyl, dodecyl, tridecyl, tetradecyl, pentadecyl, hexadecyl, heptadecyl, octadecyl, escosyl, docosyl, etc. for example having about 1-25 or more carbons such as from about 1-18 carbons, but preferably about 1-12 carbons. The term "alkyl" also includes isomers of the straight chain where branching occurs.

Cycloalkyl includes cyclopentyl, cyclohexyl, etc. and derivatives thereof such as alkyl cyclohexyl, dialkyl-cyclohexyl, etc.

Aryl, alkaryl and aralkyl include phenyl, alkylphenyl, polyalkylphenyl, chlorophenyl, alkoxyphenyl, naphthyl, alkylnaphthyl, etc., benzyl, substituted benzyl, etc.

The joining of the R groups into a ring structure include those structures derived from reactants of the general formula

such as cyclohexanone, cyclopentanone, substituted derivatives thereof such as alkyl-cyclohexanone, dialkyl-cyclohexanone.

In general, the catalyst employed herein is a sulfur or a sulfur-containing compound. The preferred catalyst is carbon disulfide or the reaction product of $CS_2$ with an amine to yield an xanthate of the general formula

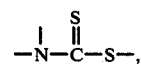

particularly as a salt thereof.

The groups substituted on the nitrogen of the xanthate can vary widely for example, alkyl, cycloalkyl, aryl, alkaryl, aralkyl, heterocyclic, etc.

The salt moiety can also vary widely for example alkali metal Na, K, Li, etc., alkali earth, Ca, etc., metal, $NH_4$, amine, etc.

In the preferred embodiment, $CS_2$ forms an xanthate inner salt with the tetrahydropyrimidines of this invention such as

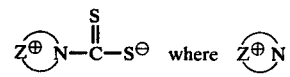

represents the tetrahydropyrimidine ring having a charged amino group for example

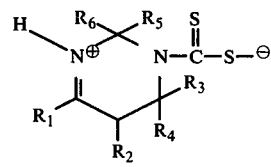

The catalyst is employed in a concentration of at least about 0.05 mole percent of the reactants, such as from about 0.05-3.0 mole percent, for example from about 0.1 to 2.0 mole percent, but preferably from about 0.3 to 0.5 mole percent. Larger amounts can be employed, if desired, but there is generally no advantage in doing so.

In general, the reaction, which is mildly exothermic, is carried out at ambient temperatures. Although elevated temperatures can be employed, the reaction is generally carried out at room temperature. Although elevated pressures can be employed such as from 0-100 psi, the reaction can be carried out at atmospheric pressure.

The following equations illustrate the preparation of derivatives of the compositions of this invention:

The substituted 2, 3, 4, 5 tetrahydropyrimidines of this invention are useful as intermediate for the preparation of N-dithiocarboxylates. Reaction of the substituted 2, 3, 4, 5 tetrahydropyrimidines with carbon disulfide yielded 1:1 adducts.

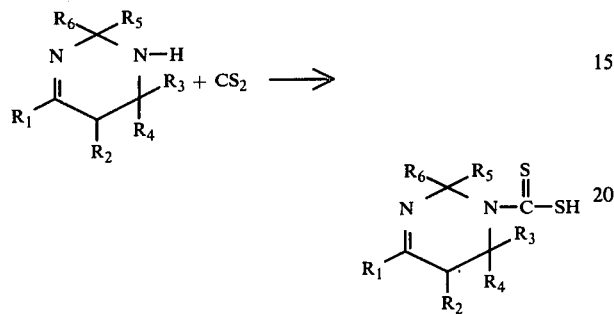

These adducts are efficient corrosion inhibitors in acid systems.

2. The tetrahydropyrimidinines can be isomerized from 2, 3, 4, 5 to 1, 4, 5, 6 tetrahydropyrimidines

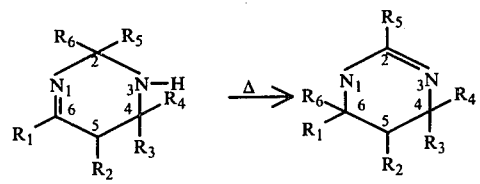

In this reaction it is required that $R_6$ by hydrogen. These are useful as corrosion inhibitors.

3. The tetrahydropyrimidines can be converted to substituted pyridines.

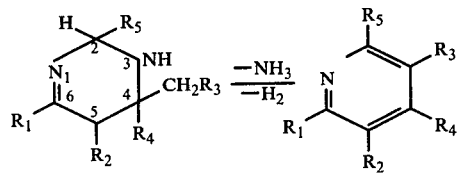

For this reaction, the 2 position contains at least 1 hydrogen and one of the groups attached to carbon 4 has at least a methylene group. These are useful as bactericides.

The following examples are presented for purpose of illustration and not of limitation.

EXAMPLE 1

4.4.6 - Trimethyl - 2,3,4,5 - tetrahydropyrimidine

A sample of 392 g. of mesityloxide and 800 cc. of 28% aq. ammonium hydroxide were stirred in a closed reaction vessel for 3 hours. The mixture was allowed to stand for 15 hours at ambient temperature. To the solution was added over a ½ hour period 300 cc. of an aq. 37% solution of formaldehyde. The temperature of the reaction mixture rose to 64° C. during the addition. After the addition was completed the mixture was stirred for 3 hours. Distillation of the reaction product yielded 419 g. (84% of theory) of 4.4.6 - trimethyl - 2,3,4,5 tetrahydropyrimidine as a colorless liquid; $b_{15}$ 62–65° C.; infrared spectrum, 3.08 m $\mu$, weak (N—H) and 6.02 m $\mu$, strong (C=N); nuclear magnetic resonance spectrum, $\tau$ in ppm, no solvent; 5.62 multiplet 2H; 8.14 multiplet + singlet 5H; 9.02 singlet 6H; and 7.72 singlet 1H.

Anal. Calc.ed for $C_7H_{14}N_2$ : N, 22.22. Found: N, 21.89.

EXAMPLE 2

2.4.4.6 - Tetramethyl - 2,3,4,5 - tetrahydropyrimidine

In a manner as described in example 1, a sample of 98 g. of mesityloxide; 200 cc. of 28% aq. ammonium hydroxide; and 50 g. of acetaldehyde yielded 120.5 g. (86% of theory) of 2.4.4.6 -tetramethyl - 2,3,4,5 tetrahydropyrimidine as a colorless liquid; $b_{15}$ 68–72° C.; infrared spectrum 3.06 m $\mu$ weak (N—H) and 6.02 m $\mu$ strong (C—N); nuclear magnetic resonance spectrum, $\tau$ in ppm, no solvent; 5.68 multiplet 1H; 8.15 singlet 3H, 8.20 singlet 2H; 8.77 doublet 3H; 8.93 singlet 3H; 9.04 singlet 3H; and 8.41 singlet 1H.

Anal. Calc.ed for $C_8H_{16}N_2$ : N, 20.00. Found: N, 19.89.

EXAMPLE 3

2 - n - Propyl - 4.4.6 - trimethyl - 2,3,4,5 - tetrahydropyrimidine

In a 1 pint pressure reactor was placed 98 g. of mesityloxide and 72 g. of butyraldehyde. Over a 5 hour period a sample of 50.6 g. of ammonia gas was introduced at such a rate that the pressure did not rise above 56 psi, After the addition was completed, stirring was continued for 17 more hours. The reaction product was dissolved in benzene and the aqueous layer, 34 cc. was separated. The benzene layer was evaporated under diminished pressure to yield 178.9 g. of an oil. Distillation of the oil under diminished pressure yielded 141 g. (84% of theory) of 2-n-propyl-4.4.6 - trimethyl -2,3,4,5 - tetrahydropyrimidine, $b_{20}$ 78–90° C.; infrared spectrum 3.06 m $\mu$ weak (N—H) and 6.01 m $\mu$ strong (C=N)

Anal. Calc.ed for $C_{10}H_{20}N_2$ : N, 16.65. Found: N, 16.53.

In a fashion as described in example 3, the following 2-substituted 4.4.6 -trimethyl - 2,3,4,5 tetrahydropyrimidines listed in Table I were prepared from mesityloxide, ammonia gas and an aldehyde.

Table I

| | | 2-Substituted - 4.4.6 - trimethyl - 2,3,4,5 - tetrahydropyrimidines from mesityloxide, ammonia gas and an aldehyde | | | | | | |
|---|---|---|---|---|---|---|---|---|
| Example no. | Mesityl- oxide grams | Aldehyde | Alde- hyde grams | Ammonia grams | Reaction time hours | Maxi- mum pres- sure psi | 2-substi- ent in Product | Yield of theory |
| 4 | 98 | n-heptaldehyde | 114 | 44 | 21 | 60 | n-hexyl | 90 |
| 5 | 98 | 2-ethylbutyraldehyde | 100 | 49 | 20 | 55 | 3-n-pentyl | 90 |

Table I-continued

2-Substituted - 4.4.6 - trimethyl - 2,3,4,5 - tetrahydropyrimidines from mesityloxide, ammonia gas and an aldehyde

| Example no. | Mesityloxide grams | Aldehyde | Aldehyde grams | Ammonia grams | Reaction time hours | Maximum pressure psi | 2-substituent in Product | Yield of theory |
|---|---|---|---|---|---|---|---|---|
| 6 | 98 | benzaldehyde | 106 | 47 | 21 | 60 | phenyl | 96 |
| 7 | 98 | 2-ethylhexanal | 128 | 43 | 24 | 65 | 3-n-heptyl | 88 |
| 8 | 98 | nonylaldehyde | 142 | 44 | 24 | 65 | n-octyl | 88 |

EXAMPLE 9

2.4.4.6 - Tetramethyl - 2,3,4,5 - tetrahydropyrimidine

A sample of 98 grams of mesityloxide and 100 cc. of 28% ammonium hydroxide were stirred for 18 hours. To the mixture was added 61 grams of 1-amino-ethanol (acetaldehyde-ammonia) and the mixture was heated to 50° C. After all the solid was dissolved, the mixture was allowed to cool to room temperature. Distillation of the product yielded 128 g. (91% of theory) of 2.4.4.6-tetramethyl - 2,3,4,5-tetrahydropyrimidine identical to the product described in example 2.

EXAMPLE 10

2.2.4.4.6 - Pentamethyl - 2,3,4,5 - tetrahydropyrimidine

In a pressure reactor was placed a mixture of 196 grams of mesityloxide and 137 grams of acetone. Over a 5 hour period 88 grams of ammonia gas was introduced at such a rate that the autogeneous pressure did not exceed 70 psi. After the addition was completed, the mixture was stirred for 18 more hours. The resulting reaction product was distilled under diminished pressure and the product $b_{20}$ 63–66° C., 265 g. (86% of theory) of 2.2.4.4.6 - pentamethyl - 2,3,4,5 - tetrahydropyrimidine was collected; infrared spectrum 3.06 m $\mu$ weak (N—H) and 6.02 m $\mu$ strong (C—N); nuclear magnetic resonance spectrum $\tau$ in ppm, no solvent, 8.12 singlet and 8.16 singlet 5H; 8.72 singlet 6H; and 8.96 singlet 6H.

Anal. Calc.ed for $C_9H_{18}N_2$: N, 18.18. Found: N, ;b 17.97.

As described in example 10, the following 2.2 disubstituted 4.4.6 trimethyl - 2,3,4,5 tetrahydropyrimidines, listed in Table II were prepared from mesityloxide, ammonia gas and a ketone.

EXAMPLE 14

2.2 Pentamethylene - 4.4.6 - trimethyl - 2,3,4,5 - tetrahydropyrimidine

A mixture of 98 grams of mesityloxide; 98 grams of cyclohexanone, 100 grams of methanol and 200 cc. of 28% aq. ammonium hydroxide was stirred for 19 hours at ambient temperature. The mixture was evaporated under diminished pressure and the resulting 178 grams of product distilled under diminished pressure to yield 164 grams (84.5% of theory) of 2.2-pentamethylene - 4.4.6 -trimethyl- 2,3,4,5 - tetrahydropyrimidine identical to the product described in example 12; infrared spectrum, 3.04 m $\mu$ N—H (weak) and 6.02 m $\mu$ C=N (strong); nuclear magnetic resonance spectrum; $\tau$ in ppm, no solvent; 8.12 singlet 3H; 8.18 singlet 2H; 8.47 broad singlet 10H; and 8.97 singlet 6H.

Anal. Calc.ed for $C_{12}H_{22}N_2$: N, 14.43. Found: N, 14.30.

EXAMPLE 15

2.4-Dipentamethylene-5,6-tetramethylene-2,3,4,5-tetrahydropyrimidine

To a stirred mixture of 98 grams of cyclohexanone and 93 grams of 28% aq. ammonium hydroxide was added 0.7 cc. of carbon disulfide. The mixture was stirred for 15 more minutes and an additional 0.7 cc. of carbondisulfide was added. Stirring was continued for 16 more hours. The mixture was evaporated under diminished pressure and the residue distilled from solid potassium hydroxide to yield 73 grams (80% of theory) of 2.4-dipentamethylene-5,6-tetramethylene-2,3,4,5-tetrahydropyrimidine as a viscous liquid $b_{0.8}$ = 186°–188° C., which slowly solidified upon standing; infrared spectrum 3.02 m $\mu$ weak (N—H) and 6.02 m $\mu$ strong (C=N).

Anal. Calc.ed for $C_{18}H_{30}N_2$: N, 10.20. Found: N, 9.88.

As described in example 15, 2.4-Dipentamethylene-5,6-tetramethylene-2,3,4,5-tetrahydropyrimidine was produced from cyclohexanone, aq. 28% ammonium hydroxide and carbon disulfide as the catalyst, in varied ratios of reactants. The results are collected in Table III.

Table II 2.2.-Disubstituted 4.4.6 - trimethyl - 2,3,4,5 - tetrahydropyrimidines from mesityloxide, ammonia gas a ketone.

| Ex. No. | Mesityloxide grams | Ketone | Ketone grams | Ammonia grams | 2.2 disubstituents | boiling point ° C. | Nitrogen Cal. | Anal. Found | % Yield of theory |
|---|---|---|---|---|---|---|---|---|---|
| 11 | 98 | methylethyl ketone | 72 | 34 | methyl ethyl | $b_{0.8}$ = 38–40 | 16.65 | 16.50 | 84 |
| 12 | 83 | cyclohexanone | 83 | 51 | pentamethylene | $b_{1.0}$ = 78–80 | 14.43 | 14.33 | 84 |
| 13 | 98 | 4-methylcyclohexamine | 112 | 44 | 5'methyl pentamethylene | $b_{20}$ = 115–121 | 13.46 | 13.51 | 86 |

Table III

Formation of 2.4 - Dipentamethylene - 5.6 - tetramethylene - 2,3,4,5 - tetrahydropyrimidine from cyclohexanone, 28% aq. ammonium hydroxide and carbon disulfide

| Ex. No. | Cyclohex-anone grams | 28% aq. Ammonium hydroxide grams | Carbon disulfide grams | Reaction time-hrs. | % Yield of theory |
|---|---|---|---|---|---|
| 16 | 49 | 72 | — | 18 | 6 |
| 17 | 49 | 20 | 0.6 | 18 | 53 |
| 18 | 49 | 30 | 1.2 | 18 | 66 |
| 19 | 49 | 40 | 1.2 | 18 | 76 |
| 20 | 49 | 36 | 1.2 | 18 | 76 |
| 21 | 49 | 45 | 0.8 | 18 | 78 |
| 22 | 49 | 20 | 0.6 + 0.6* | 18 | 80 |
| 23 | 49 | 72 | 0.4 + 0.3* | 18 | 81 |

*Catalyst added in two portions at 15 minutes interval.

EXAMPLE 24

Trimethyl 2.4-Dipentamethylene-5,6-tetramethylene-2,3,4,5 tetrahydropyrimidine

In a pressure reactor was placed 112 grams of 3-methylcyclohexanone and 2 grams of carbon disulfide. To the mixture was added over a 4 hour period 14 grams of ammonia gas. After the addition was completed the mixture was stirred for 18 more hours at ambient temperature. The aqueous phase which separated, 17.8 cc., was removed and the product distilled over potassium hydroxide under diminished pressure. The trimethyl 2.4-dipentamethylene-5.6-tetramethylene-2,3,4,5-tetrahydropyrimidine was collected as 76.5 g. (73% of theory) of a very viscous liquid.

EXAMPLE 25

Carbon disulfide adduct of 2.4-Dipentamethylene-5.6-tetramethylene-2,3,4,5-tetrahydropyrimidine A sample of 27.4 grams of 2.4-dipentamethylene-5,6-tetramethylene-2,3,4,5-tetrahydropyrimidine was dissolved in 250 cc. of ether. To the solution was added 10 grams of carbon disulfide and the mixture was allowed to stand for 16 hours. The bright yellow solid which precipitated was filtered off and washed one time with ether. The product was air dried to yield 34.5 grams (98.5% of theory) of the carbon disulfide adduct of 2.4-dipentamethylene-5.6-tetramethylene 2,3,4,5-tetrahydropyrimidine, m.p. 122°–124° C.

Anal. Calc.ed for $C_{19}H_{30}N_2S_2$: N, 8.0 : S, 17.8. Found: N, 8.1 : S, 18.3.

EXAMPLE 26

2.4-Dipentamethylene-5.6-tetramethylene-2,3,4,5-tetrahydropyrimidine

In a pressure reactor was placed 49 grams of cyclohexanone and 1 gram of carbon disulfide. Over a 4½ hour period 7.5 grams of ammonia gas was introduced. After the addition was completed the mixture was stirred for 3 more hours. The aqueous layer (8.1 cc.) was separated by extraction of the product in ether. The ethereal solution was evaporated and the resulting product distilled under diminished pressure to yield 40 grams (87.5% of theory) of 2.4-dipentamethylene-5.6-trimethylene-2,3,4,5-tetrahydropyrimidine, identical to product described in example 15.

EXAMPLE 27

Carbon disulfide adduct of 2.4-Ditetramethyne-5.6-trimethylene-2,3,4,5-tetrahydropyrimidine Into a mixture of 84 grams of cyclopentanone, 2 grams of carbon disulfide and 50 grams of methanol was introduced over a 3-½ hour period 18.2 grams of ammonia gas. After the addition was completed the mixture was stirred for 15 more hours at ambient temperature. The solvent was removed under diminished pressure and the resulting product was distilled under diminished pressure. A sample of 18 grams of the distilled product was dissolved in 100 cc. of ether and 40 grams of carbon disulfide was added. The mixture was allowed to stand at room temperature for 1 hour and the solid which precipitated was filtered off and washed with ether. The yellow solid was air dried to yield 9.0 grams of the carbon disulfide adduct of 2.4-ditetramethylene-5.6-trimethylene-2,3,4,5-tetrahydropyrimidine, m.p. 105°–108° C.

Anal. Calc.ed for $C_{16}H_{24}N_2S_2$: N, 9.1; S, 20.8. Found: N, 9.35; S, 23.0.

EXAMPLE 28

2.2.4.4.6-Pentamethyl-2,3,4,5-tetrahydropyrimidine

In a pressure reactor was placed 174 grams of acetone and 1.54 grams of the carbon disulfide adduct 2.4-dipentamethylene-5,6-tetramethylene-2,3,4,5-tetrahydropyrimidine, described in example 25. To the mixture was added 30.4 grams of ammonia gas over a 4 hour period at such a rate that the autogeneous pressure did not exceed 60 psi. After the addition was completed the mixture was stirred for 70 more hours. Distillation yielded 90 grams (59% of theory) of 2.2.4.4.6-pentamethyl-2,3,4,5-tetrahydropyrimidine identical to the product described in example 10.

In a fashion as described in example 28, 2.2.4.4.6-Pentamethyl 2,3,4,5-tetrahydropyrimidine was prepared from acetone, ammonia gas and a catalyst under various conditions. The results are summarized in Table IV.

Table IV 2.2.4.4.6 Pentamethyl-2,3,4,5 tetrahydropyrimidine from acetone and ammonia

| Ex. No. | Acetone grams | Ammonia grams | Catalyst as prepared in example 28 | Catalyst grams | Reaction time hours | Reaction Temperature ° C. | Maximum pressure psi | Percent yield of theory |
|---|---|---|---|---|---|---|---|---|
| 29 | 174 | 50 | none | none | 21 | 25–29 | 58 | 5 |
| 30 | 174 | 37 | 25 | 0.77 | 21 | 26–34 | 48 | 55 |
| 31 | 174 | 50 | 25 | 1.54 | 70 | 25–35 | 44 | 65 |
| 32 | 174 | 38 | 25 | 2.32 | 21 | 25–35 | 42 | 66 |
| 33 | 174 | 37 | 25 | 3.12 | 21 | 28–36 | 43 | 69 |
| 34 | 174 | 38 | 27 | 0.77 | 67 | 25–33 | 48 | 66 |

EXAMPLE 34A 2,4-Di-n-propyl-5-ethyl-2,3,4,5-tetrahydropyrimidine

In a pressure reactor was placed 72 grams of butyraldehyde and 6 grams of ammonium chloride. To the mixture was added over a half hour period 23 grams of ammonia gas. After the addition was completed the mixture was stirred for 23 more hours at ambient temperature. Ether was added to facilitate separation of the aqueous phase. The ethereal solution was evaporated under diminished pressure to yield 64.9 grams (99% of theory) of 2.4-di-n-propyl-5-ethyl-2,3,4,5-tetrahydropyrimidine; infrared spectrum 3.08 m μ (weak) and 6.08 m μ strong absorption.

Anal. Calc.ed for $C_{12}H_{24}N_2$: N, 14.28. Found: N, 14.05.

EXAMPLE 35

2-Phenyl-4.4.6-trimethyl-3,4,5,6-tetrahydropyrimidine

A sample of 180 grams of 2-phenyl-4.4.6-trimethyl-2,3,4,5-tetrahydropyrimidine was distilled under diminished pressure over 10 grams of potassium hydroxide. The fraction 69 grams of $b_{0.8}$ = 123°–150° C., which solidified during the distillation, as collected. Crystallization yielded 2-phenyl-4.4.6-trimethyl-3,4,5,6-tetrahydropyrimidine as a white solid, m.p. 86°–87° C.; infrared spectrum 3.06 m μ weak (N—H) and 6.20 m μ strong (C=N), nuclear magnetic resonance spectrum, τ in ppm, solvent $CHCl_3$, 2.28 multiplet 2H; 2.65 multiplet 3H; 4.93 singlet 1H; 6.61 multiplet 1H; 8.42 multiplet 2H; 8.81 doublet 3H; 8.82 singlet 3H; and 8.92 singlet 3H.

Anal. Calc.ed for $C_{13}H_{18}N_2$: N, 13.86. Found: N, 13.6.

EXAMPLE 36

Glyoxal, mesityloxide, ammonia condensate

A sample of 98 grams of mesityloxide and 200 cc. of 28% ammonium hydroxide was stirred for 3 hours. To the mixture was added 72.5 grams of a 40% aq. glyoxal solution. The mixture was stirred for ½ hour at ambient temperature and evaporated under diminished pressure. There was isolated 65 grams of a red viscous liquid.

Anal. Calc.ed for $(C_7H_{13}N_2)_x$: N, 22.3. Found: N, 21.9.

EXAMPLE 37

2.4.6-Collidine

A sample of 54.8 grams of 2.4.4.6-tetramethyl-2,3,4,5-tetrahydropyrimidine was heated for 23 hours at reflux temperature, 168°–179° C. to yield 41.3 g. of a red liquid.

Anal. Calc.ed for $C_8H_{11}N$: N, 11.58. Found: N, 11.38. Distillation of the product yielded 2.4.6 collidine, $b_{20}$ = 66°–68° C. identical spectral characteristic with authentic 2.4.6 collidine.

In a fashion as described in example 37, the following 6-substituted 2.4-dimethylpyridines, collected in Table V were prepared from substituted 4.4.6 trimethyl-2,3,4,5-tetrahydropyrimidines.

Table V

| Ex. No. | Starting mtl. product from Exam. No. | Reaction time hours | Reaction Temperature ° C. | 6-Substituent in Product | Nitrogen Calc. ed | Anal. Found |
|---|---|---|---|---|---|---|
| 38 | 3 | 17 | 172–180 | n-propyl | 10.37 | 10.3 |
| 39 | 4 | 21 | 180 | n-hexyl | 7.92 | 7.8 |
| 40 | 5 | 18 | 180 | isopentyl | 8.58 | 8.3 |

EXAMPLE 41

2-n-Propyl-3.5-diethyl pyridine

Into a mixture of 62.9 grams of 2.4-di-n-propyl-5-ethyl-2,3,4,5-tetrahydropyrimidine, 4 grams of ammonium acetate and 4 grams of copper (II) acetate was introduced oxygen gas. Under continuous stirring and introduction of oxygen gas, the mixture was heated for 3 hours at 96°–128° C. The resulting reaction mixture was distilled under diminished pressure. The fraction $b_{20}$ 122°–126° was collected as 37.2 grams (67.8% of theory) of 2-n-propyl-3.5-diethyl pyridine; nuclear magnetic resonance spectrum, no solvent, τ in ppm 1.62 doublet 1H; 2.62 doublet 1H; 7.33 multiplet 6H; 8.20 multiplet 2H; 8.82 triplet and 9.03 triplet 9H.

Anal. Calc.ed for $C_{12}H_{19}N$: N, 7.91. Found: N, 7.8.

The products of the above reactions where THP's are prepared are summarized in the following table

TABLE A $$R_6\underset{N_1}{\diagdown}\overset{2}{\diagup}R_5,\ _3NH,\ R_1-\underset{R_2}{\overset{6}{|}}-\underset{R_4}{\overset{4}{|}}-R_3\ (5)$$

| Ring Position | 6 | 5 | 4 | 4 | 2 | 2 |
|---|---|---|---|---|---|---|
| Ex. Subst. Group | $R_1$ | $R_2$ | $R_3$ | $R_4$ | $R_5$ | $R_6$ |
| 1 | $CH_3$ | H | $CH_3$ | $CH_3$ | $CH_3$ | $CH_3$ |
| 2 | $CH_3$ | H | $CH_3$ | $CH_3$ | H | $CH_3$ |
| 3 | $CH_3$ | H | $CH_3$ | $CH_3$ | H | n-$C_3H_7$ |
| 4 | $CH_3$ | H | $CH_3$ | $CH_3$ | H | n-$C_6H_{13}$ |
| 5 | $CH_3$ | H | $CH_3$ | $CH_3$ | H | i-$C_5H_{11}$ |
| 6 | $CH_3$ | H | $CH_3$ | $CH_3$ | H | Phenyl |
| 7 | $CH_3$ | H | $CH_3$ | $CH_3$ | H | i-$C_7H_{15}$ |
| 8 | $CH_3$ | H | $CH_3$ | $CH_3$ | H | n-$C_8H_{17}$ |
| 9 | $CH_3$ | H | $CH_3$ | $CH_3$ | H | $CH_3$ |
| 10 | $CH_3$ | H | $CH_3$ | $CH_3$ | $CH_3$ | $CH_3$ |
| 11 | $CH_3$ | H | $CH_3$ | $CH_3$ | $CH_3$ | $C_2H_5$ |
| 12 | $CH_3$ | H | $CH_3$ | $CH_3$ | —$(CH_2)_5$— | |
| 13 | $CH_3$ | H | $CH_3$ | $CH_3$ | —$(CH_2)_2$—C—$(CH_2)_2$— \| $CH_3$ | |
| 14 | $CH_3$ | H | $CH_3$ | $CH_3$ | —$(CH_2)_5$— | |
| 15–23 | —$(CH_2)_4$— | | —$(CH_2)_5$— | | —$(CH_2)_5$— | |

TABLE A-continued

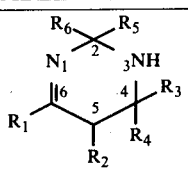

| Ex | Ring Position | 6 | 5 | 4 | 4 | 2 | 2 |
|---|---|---|---|---|---|---|---|
| | Subst. Group | $R_1$ | $R_2$ | $R_3$ | $R_4$ | $R_5$ | $R_6$ |
| 24 | | —(CH$_2$—C(CH$_3$)—(CH$_2$)$_2$— | | —CH$_2$—C(CH$_3$)—(CH$_2$)$_3$— | | —CH$_2$—C(CH$_3$)—(CH$_2$)$_3$— | |
| 26 | | —(CH$_2$)$_4$— | | —(CH$_2$)$_5$— | | —(CH$_2$)$_5$— | |
| 28–34 | | CH$_3$ | H | CH$_3$ | CH$_3$ | CH$_3$ | CH$_3$ |
| 34A | | H | C$_2$H$_5$ | H | n-C$_3$H$_7$ | H | n-C$_3$H$_7$ |

The compositions of this invention are useful as corrosion inhibitors, insecticides, anti-oxidants, biocides including bacterocides, fungicides, etc.

The xanthates, besides being useful as a catalyst for the preparation of the tetrahydro pyrimidines of this invention, are also useful as corrosion inhibitors, oxygen scavengers, biocides, insecticides, etc.

The compositions of this invention can be converted to a wide variety of derivatives including salts, quaternaries, isomerized pyrimidines, pyridines, etc.

I claim:

1. A process of preparing 2,3,4,5-tetrahydropyrimidines which comprises reacting at ambient temperatures and pressures a carbonyl compound from the group consisting of aldehydes and ketones with ammonia or ammonium hydroxide in the presence of 0.1 to 2.0 mole percent, based upon the reactants of carbon disulfide as a catalyst.

2. The process of claim 1 wherein the reaction is carried out by mixing the reactants for a period of up to 18 hours.

3. The process of claim 1 where both a ketone and an aldehyde is reacted.

4. The process of claim 3 where the ketone is mesityl oxide and the aldehyde is formaldehyde.

5. The process of claim 1 which comprises placing 3-methyl-cyclohexanone and carbon disulfide in a reactor, adding ammonia over a period of four hours, upon completion of the addition of the ammonia, stirring the mixture for a period of 18 hours and recovering the 2,3,4,5-tetrahydropyrimidine.

6. The process of preparing 2,3,4,5-tetrahydropyrimidines which comprises reacting a ketone and a carbon disulfide adduct of a 2,3,4,5-tetrahydropyrimidine with ammonia by mixing and stirring the reactants for a period of 70 hours.

7. The process of claim 6 where the ketone is acetone, the adduct is the carbon disulfide adduct of 2,4-dipentamethylene-5,6-tetramethylene-2,3,4,5-tetrahydropyrimidine and the product obtained is 2,3,4,4,6-pentamethyl-2,3,4,5-tetrahydropyrimidine.

8. The process of claim 1 where the carbonyl compound has the formula

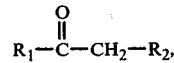

where $R_1$ and $R_2$ are hydrogen, alkyl, aryl, cycloalkyl, alkaryl, aralkyl, or heterocyclic or the R groups may be joined in a cyclic configuration.

* * * * *